(12) United States Patent
Haq et al.

(10) Patent No.: US 9,921,101 B2
(45) Date of Patent: *Mar. 20, 2018

(54) SCANNER PHOTOMETER AND METHODS

(71) Applicant: Douglas Scientific, LLC, Alexandria, MN (US)

(72) Inventors: Adnanul Haq, Alexandria, MN (US); Richard J. Schoeneck, Alexandria, MN (US)

(73) Assignee: DOUGLAS SCIENTIFIC, LLC, Alexandria, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/309,435

(22) Filed: Jun. 19, 2014

(65) Prior Publication Data

US 2015/0014551 A1    Jan. 15, 2015

Related U.S. Application Data

(63) Continuation of application No. 13/942,135, filed on Jul. 15, 2013, now Pat. No. 8,759,795, which is a continuation of application No. 13/123,100, filed as application No. PCT/US2009/060147 on Oct. 9, 2009, now Pat. No. 8,487,276.

(Continued)

(51) Int. Cl.
*G01J 1/58* (2006.01)
*G01J 3/10* (2006.01)
*G01J 3/44* (2006.01)
*G01N 21/64* (2006.01)

(52) U.S. Cl.
CPC . *G01J 1/58* (2013.01); *G01J 3/10* (2013.01); *G01J 3/4406* (2013.01); *G01N 21/645* (2013.01); *G01N 21/6452* (2013.01); *G01N 2021/6419* (2013.01); *G01N 2021/6421* (2013.01); *G01N 2021/6441* (2013.01)

(58) Field of Classification Search
CPC .... G01J 3/10; G01J 1/58; G01J 3/4406; G01J 3/6878; G01J 3/345; G01N 21/6452; G01N 2021/6419
USPC .......... 250/458.1, 459.1, 200, 461.1
See application file for complete search history.

(56) References Cited

U.S. PATENT DOCUMENTS 5,192,510 A * 3/1993 Zoha .................... G01N 21/648
356/244
5,946,431 A * 8/1999 Fernandes ............ G01N 21/253
250/458.1

(Continued)

OTHER PUBLICATIONS

Canadian Office Action for Canadian Application No. 2,740,114, dated Nov. 18, 2015, 6 pages.

*Primary Examiner* — David Porta
*Assistant Examiner* — Faye Boosalis
(74) *Attorney, Agent, or Firm* — Greenberg Traurig LLP

(57) ABSTRACT

A scanning photometer and attendant methods are provided. The scanning photometer is generally characterized by first and second fluorophore excitation sources, an objective lens, and a common emission detector for the detection of first and second fluorophore emission originating from the excitation of the fluorophores via passage of excitation energy, via an optical path of the objective lens, from the excitation sources. Excitation energy and emission energy conditioning elements are likewise provided, operatively interposed before or after the objective lens as the case may be.

21 Claims, 5 Drawing Sheets

Related U.S. Application Data

(60) Provisional application No. 61/104,109, filed on Oct. 9, 2008.

(56) References Cited

U.S. PATENT DOCUMENTS

| | | |
|---|---|---|
| 6,071,748 A | 6/2000 | Modlin et al. |
| 6,320,196 B1 | 11/2001 | Dorsel et al. |
| 2002/0109844 A1 | 8/2002 | Christel et al. |
| 2012/0080611 A1* | 4/2012 | Jones .................... G01J 1/0242 250/458.1 |

* cited by examiner

SCANNER PHOTOMETER AND METHODS

This is an international patent application filed under 35 U.S.C. § 363 claiming priority under 35 U.S.C. § 119(e)(1) to U.S. provisional pat. appl. Ser. No. 61/104,109, filed Oct. 9, 2008 and captioned "Scanner Photometer and Methods," said application incorporated herein by reference in its entirety.

TECHNICAL FIELD

The present invention generally relates to the field of optics, more particularly, to instruments and/or methods for detecting and/or measuring light intensity or optical properties of solutions or surfaces, and more particularly still, to a scanner photometer and methods having particular utility with regard to fluorescence detection and/or quantification.

BACKGROUND OF THE INVENTION

The minimization of uncertainty with regard to data is universally held as advantageous. Moreover, and fundamentally, in as much as there exists a premium on precision in acquiring data, to appreciate and acknowledge uncertainty with regard to data acquisition is likewise of value so that "meaningful" data informs the technician, clinician, scientist, engineer, etc.

Fluorescence photometry is premised upon the adsorption and subsequent re-radiation of light, i.e., electromagnetic radiation, by organic and inorganic specimens. Via fluorescence labeling or tagging of a specimen, sample, etc. with a fluorophore (a/k/a, a fluorochrome), i.e., a functional group of a molecule which absorbs energy of a specific wavelength and re-emits energy at a different, but equally specific wavelength wherein the amount and wavelength of the emitted energy depend on both the fluorophore and the chemical environment of the fluorophore; the application of excitation energy to such specimen; and, monitoring or sensing of emission energy from the excited specimen, the presence/absence and/or quantity of a tagged component of the specimen may be obtained or ascertained. Well known illustrative, non-limiting fluorescence photometry fields include, molecular biology, biochemistry, and pharmaceutical science, with particular, but hardly exclusive utility known with regard to genotyping, sequencing, screening and clinicals.

Characteristic of scanning operations is a scanner, a target, and motion of one element with respect to the other. Upon reflection, it should be appreciated that potential scanning issues arise in connection to the inherent motion of scanning, e.g., getting either the scanner or the target from point A to point B, as well as the relative positioning or alignment from one target to the next for the purpose of data acquisition.

Optical scanning heads, more particularly photometers, include components, such as photomultiplier tubes (PMTs), which are susceptible to mechanical vibration. One cause of mechanical vibration is the physical quantity known as "jerk" (J), mathematically the first time-derivative of acceleration (A), i.e., $J=dA/dt$, which is manifest or inherent in the motion cycle of a scanning carriage to which a scanning photometer is commonly attached. In an effort to eliminate jerk related vibration in or with respect to the photometer, it has heretofore been found advantageous to provide a static or stationary photometer, and a dynamic specimen medium, e.g., a selectively positionable plate, which passes thereby. With increased processing throughput via the use of continuously spooled array tape and the like, use of a stationary photometer has become impractical, however, any inconsistency in the relative position between the scanning photometer and each target of a series of targets, due to any reason, can cause significant differences in the quality of output data.

In the context of a multi-dye fluorescence assessment, the characteristic multiple fluorophore excitation energy directed to a first target, and returned fluorophore emission energy from the excited target, e.g., the paths associated therewith, must be precise, certain and repeatable/reliable in relation to the target itself, as well as from a first target to successive targets. Repeatability of data acquisition conditions is highly valued, and in the context of reduced specimen/target volumes for scanning, and with regard to the high volume throughput available with array tapes, repeatability, reliability and precision is an increasing challenge. Thus, in light of at least the forgoing, it remains advantageous to provide a scanning photometer capable of precise, reliable and repeatable data acquisition, more particularly, such scanning photometer and associated methods which complement heretofore known target media processing advancements.

SUMMARY OF THE INVENTION

A scanning photometer and attendant methods are provided. The scanning photometer is generally characterized by first and second fluorophore excitation sources, an objective lens, and a common emission detector for the detection of first and second fluorophore emissions originating from the excitation of the fluorophores via passage of excitation energy, via an optical path of the objective lens, from the excitation sources. Excitation energy and emission energy conditioning elements are likewise provided, operatively interposed before or after the objective lens as the case may be.

The scanning photometer is advantageously operatively supported by a scanning rail carriage for reversible travel. More particularly, travel characterized by a constant velocity during active scanning of targets of an array of targets. Moreover, the scanning photometer may further advantageously include a third fluorophore excitation source, excitation energy therefrom passing through the objective lens, and a further emission detector for the detection of fluorophore emissions originating from excitation of the third fluorophore.

In connection to photometric scanning methods, those of the instant invention may be fairly and generally characterized by the steps of passing an objective lens across a series of spaced apart targets, and transmitting energy from at least two fluorophore excitation sources through an optical path of the objective lens for receipt by a target of a series of spaced apart targets in furtherance of exciting at least two fluorophores of the target. Advantageously, but not necessarily, the objective lens is passed across the series of spaced apart targets at a constant velocity. Moreover, during a "pass," energy transmissions directed to the target from the fluorophore excitation sources may be simultaneous, periodic, alternated (i.e., transmission from a first source; transmission from a second source upon termination of the first source transmission; and, a return to first source transmission upon termination of the second source transmission), or pulsed (i.e., transmission from one source of the two sources is pulsed during the energy transmission of another of the two sources).

Broadly, and as will be later detailed, there are provided preferred optical operational modalities for a multi-dye scanning photometer, namely, multi-dye measurements characterized by notions of "colocalization" (i.e., obtaining independent measurements simultaneously at a common localized alignment), "consensing" (i.e., use of a single emission detector for the detection of two fluorophore emissions), "consituational" (i.e., the elimination or minimization of different situational relationships or inherent conditions for the specimen between measurements), and "confocal" (i.e., establishing a common local alignment for and/or between the specimen focal point and the aperture focal point).

More specific features and advantages obtained in view of those features will become apparent with reference to the drawing figures and DETAILED DESCRIPTION OF THE INVENTION.

DETAILED DESCRIPTION OF THE INVENTION

Figure 1:
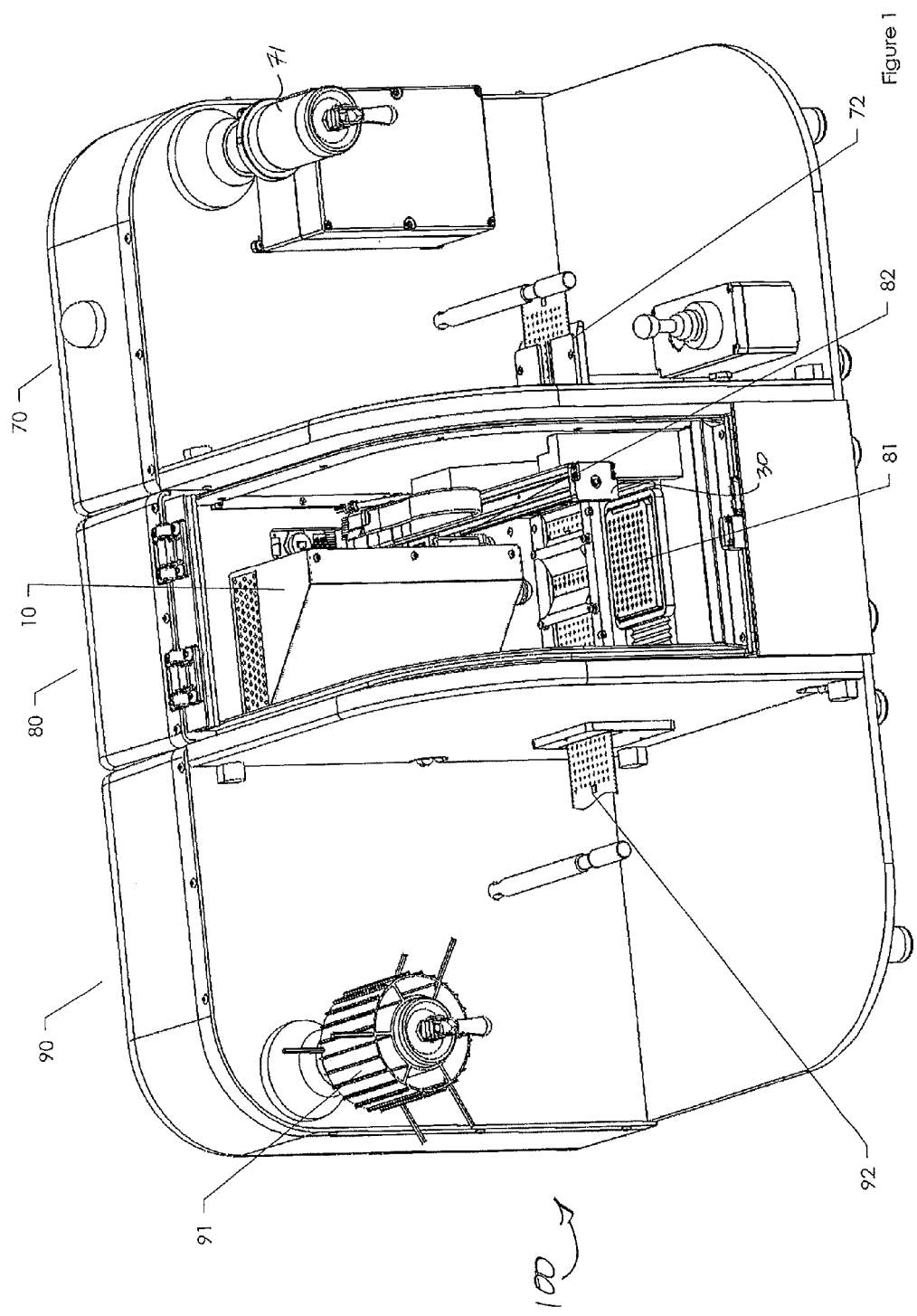
FIG. 1 depicts, in perspective view, a scanning photometer apparatus characterized by a scanning photometer in accord with a preferred teaching of the instant disclosure, a scanning module door omitted to show underlaying structures.
Figure 2:
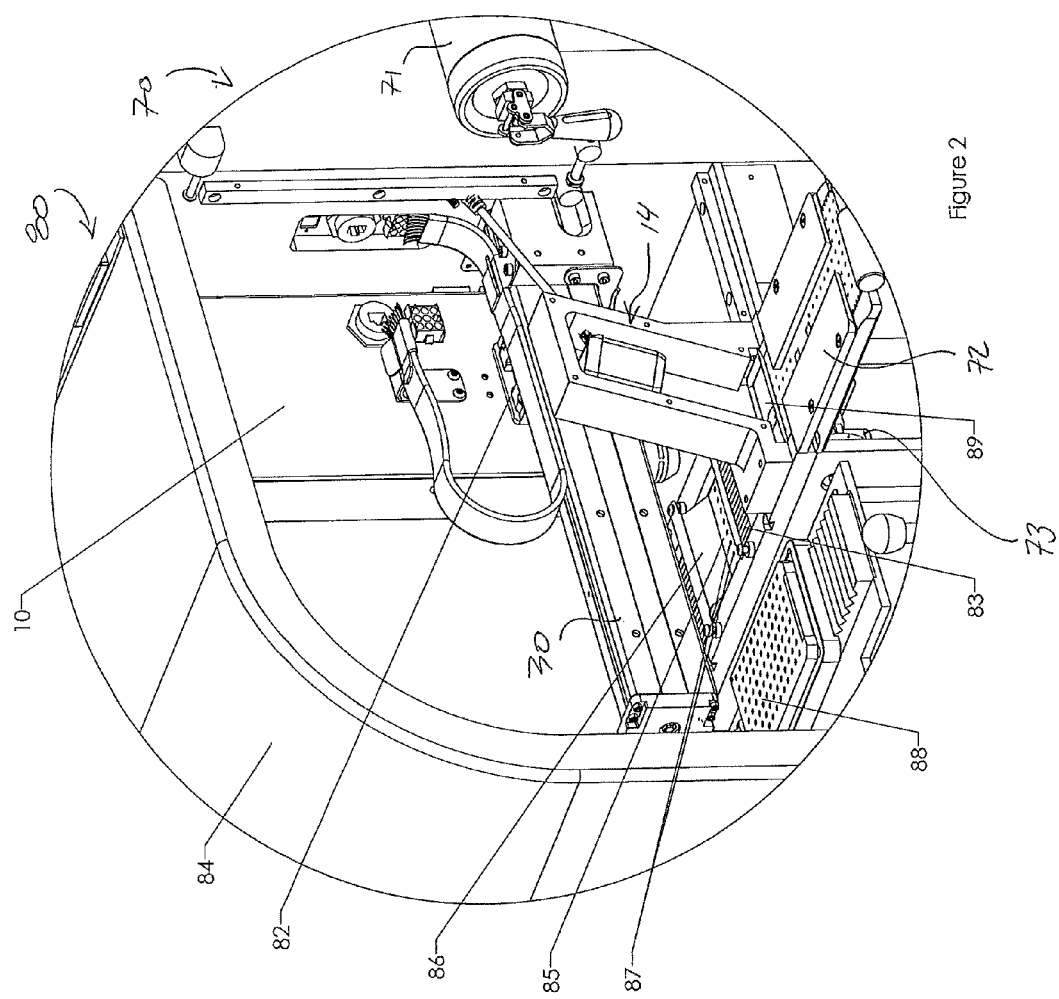
FIG. 2 depicts, in perspective view with portions omitted for the sake of clarity, elements of the scanning photometer apparatus of FIG. 1 and their interrelationships as viewed from the vantage point of the unwind module.
Figure 3:
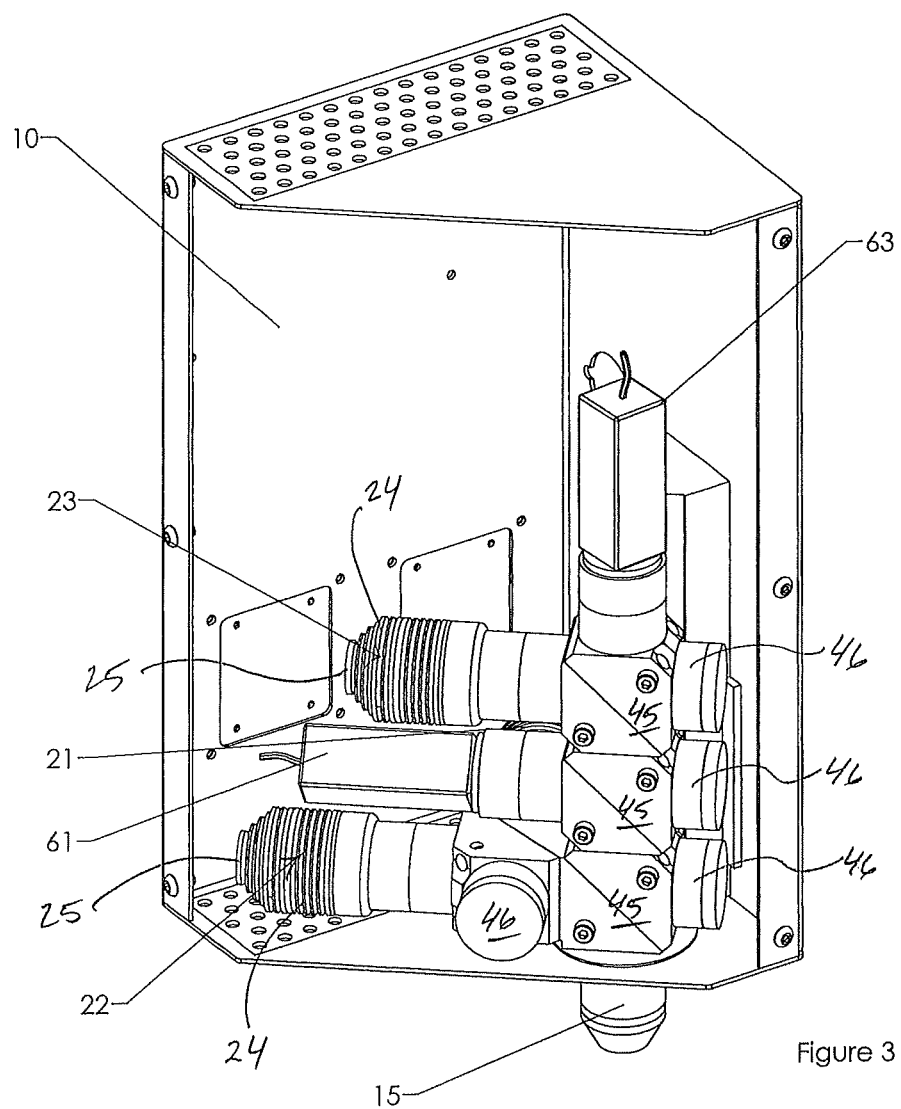
FIG. 3 depicts, in perspective view, operative elements of the scanning photometer of FIG. 1.
Figure 4:
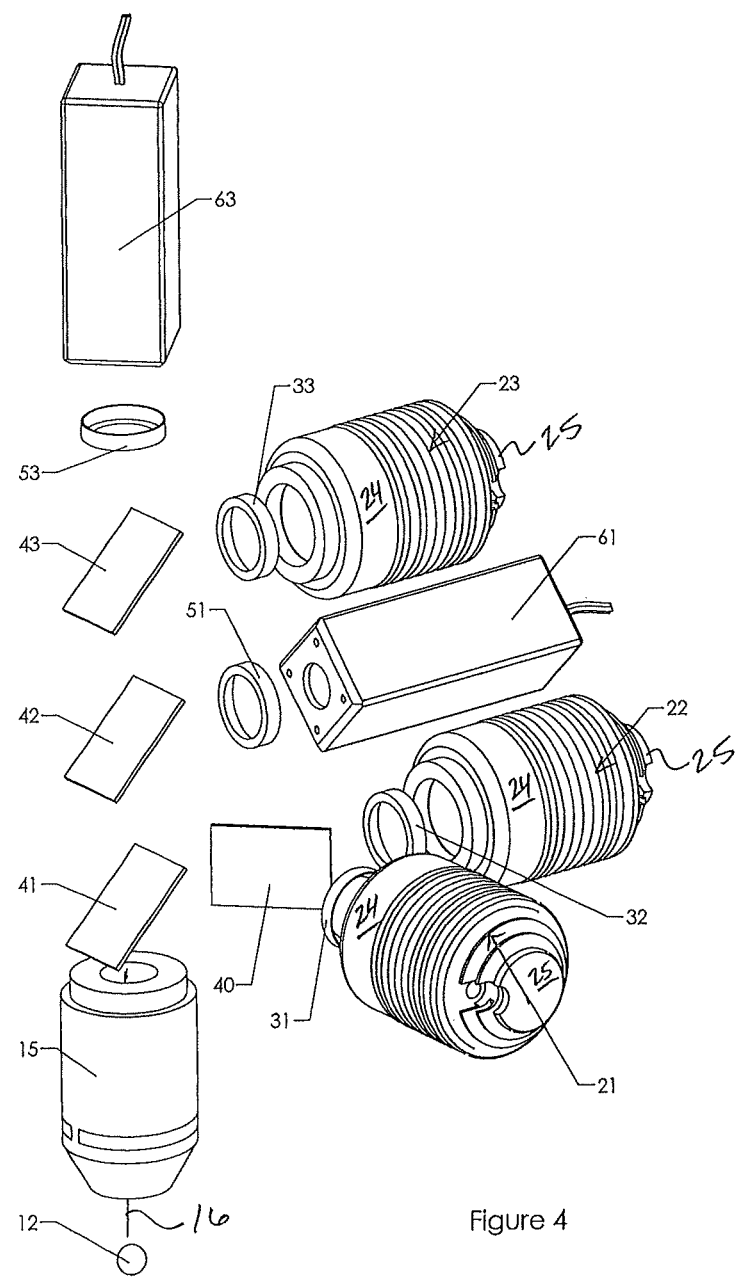
FIG. 4 depicts, in exploded view, select elements of the scanning photometer of FIG. 3; and, FIG. 5 represents a motion profile, more particularly, an acceleration profile of the scanning photometer of FIG. 1.

The following description immediately proceeds with general reference to FIGS. 1 & 2, wherein a preferred, non-limiting scanning photometer apparatus is generally depicted, and thereafter with particular reference to FIGS. 3 & 4 wherein an optical reader or optical reader head of the subject apparatus is depicted. Finally, reference is made to FIG. 5 with regard to preferred apparatus operation.

Contextually, the apparatus of FIGS. 1 & 2 is advantageously, but not exclusively suited for high speed scanning, derived, at least in part, from the utilization of array tape (see e.g., U.S. Pat. No. 6,878,345 B1) and an automated system/process for/of handling same (see e.g., the Nexar™ array tape automation instrument by Douglas Scientific, Minnesota, USA). Moreover, while the subassembly of FIGS. 3 & 4 may be generally and fairly characterized as an optical reader head, it may be more particularly and fairly characterized as a multi-dye fluorescence photometer, having particular utility with regard to, for example and without limitation, single nucleotide polymorphisms (SNP) genotyping via allele specific polymerase chain reaction (PCR) assays (see e.g., U.S. Pat. Nos. 6,537,752 B1 and 6,632,653 B1) as well as emerging related processes, see e.g., Applicant's copending international patent application ser. no. PCT/US09/42007 entitled "High Throughput Screening Employing Combination of Dispensing Well Plate and Array Tape."

With reference now to FIGS. 1 & 2, a scanner photometer apparatus 100 according to the preferred teachings of the present invention is shown, and generally includes an unwind module 70, a scanning module 80, and a rewind module 90. In the unwind module 70, the spool holder 71 holds tape 92, in spool form, which is characterized by an array of "wells" (i.e., rows and columns of spaced apart aqueous volumes set across the length and width of the tape respectively). The tape 92 feeds off spool holder 71 into the tape guide 72, and onto a tape drive 73 which conveys the tape 92 toward and through the scanning module 80. The tape 92 is indexingly conveyed via tape drive 73 so as to stop for scanning by the optical reader head 10, more particularly, column scanning as depicted.

A bar code reader/reading station 14 (FIG. 2), characterized by, among other things, a bar code hold down 89, is advantageously supplied for detecting and "reading" sample/well indicia associated with the conveyed tape or tape segment in furtherance of correlating a select photometric scanning result with a select target sample (i.e., target well). Light from the bar code reader of the reading station is generally shielded from photometric scanning operations by at least a portion of the bar code reading station, e.g., the bar code hold down 89.

The tape is generally held flat in tape scanning region 85 by a tape hold down 86, with light from the region advantageously shielded by dark enclosure 84 (FIG. 4). Moreover, the tape hold down acts as a funnel guide for the ends of the tape, and further shields bar code scanning emissions from photometric scanning operations of the scanning module. Tape hold down 86, characterized by apertures 87 configured so as to correspond or register with well locations of the conveyed tape, is advantageously, but not necessarily, comprised of a resilient member or element, or is otherwise adapted so as to automatically compensate for or respond to tape thickness variations while nonetheless maintaining a surface of the tape in operative engagement with groove plate 83.

With regard to the scanning module 80, a movable carriage 82, to or upon which the optical reader head 10 is operatively mounted, is translatable upon a carriage rail 30 or the like such that the optical reader head passes through tape scanning region 85. The optical reader head is advantageously designed to be easily connected with the scanning rail carriage. As should be readily appreciated with reference to the figures, the motion of the carriage, and thus the optical reader head, is perpendicular to the tape drive motion, and parallel to the top surface or face of groove plate 83.

Functionally, the optical reader head 10 moves in a first direction as it scans each well in the target column. Once the target column is scanned, the tape 92 indexes ahead one column, thereby establishing a new target column, and the optical reader head 10 moves in a second direction as it scans each well in the subsequent target column, with the feeding/indexing and scanning process repeating. As the tape 92 indexes, it winds on the rewind or uptake spool 91.

In lieu of tape processing via a tape drive, plate processing is enabled via a plate drive. Plate 81, likewise characterized by an array of wells, can be manually loaded or conveyed into the scanning module 80, more particularly, provided to or within a plate scanning region 88 which is oriented with respect to tape scanning region 85 so as to be in-line therewith. Plate motion is generally parallel to the motion of the tape, with a top or upper surface of the plate generally parallel to an upper or top surface of the tape. Similar to tape processing, the optical reader head 10 scans a target column of the plate 81 in a first direction, and, thereafter, and subsequent to manipulation of the plate 81 as by manual indexing forward one column, the optical reader head 10 then reads the new target column in a second direction, with the process repeating.

With reference now to FIG. 3, and the particulars of FIG. 4, there is depicted multiple excitation sources, with attendant excitation energy conditioning elements; dual emission detectors, with attendant emission energy conditioning elements; and, an objective lens characteristic of the optical scanning head, more particularly, the multi-dye fluorescence photometer of the instant invention. The photometer of FIG. 3, and as best seen in connection to FIG. 4, advantageously, but not necessarily, includes first 21, second 22 and third 23 fluorophore excitation sources, an objective lens 15, characterized by an optical path 16, through which excitation energy from the fluorophore excitation sources pass, and, first 61 and second 63 emission detectors for selectively detecting fluorophore emissions originating from excitation of fluorophores of a target. Advantageously, detection of greater than one fluorophore emission by a single emission detector provides improved scanning precision and an accompanying upgrade with regard to data quality.

Excitation energy conditioning elements are operatively interposed between the excitation sources and the objective lens. More particularly, excitation energy conditioning elements comprise, in selective combination, excitation filters and beam splitters for select passage of excitation energy to and along the optical path of the objective lens.

As shown, and to facilitate subsequent discussion, excitation energy filters 31, 32, and 33 correspond to first 21, second 22 and third 23 fluorophore excitation sources. With regard to the excitation energy beam splitters, splitters 40, 41, 42 & 43 are provided for conditioning excitation energy from fluorophore excitation sources 21, 22, & 23. As will be subsequently addressed in connection to emission energy conditioning, excitation energy beam splitters 41 & 43 are arranged so as to likewise selectively condition fluorophore emissions.

Emission energy conditioning elements are likewise operatively interposed between the objective lens and the emission detectors. More particularly, emission energy conditioning elements comprise, in selective combination, beam splitters, dedicated and shared, and emission filters for select passage of emission energy from the optical path of the objective lens and to the emission detector.

As shown, emission energy beam splitter 42 is provided, and is generally correlated with/to first emission detector 61, with splitters 41 & 43 conditioning emission energy directed toward second emission detector 63, and splitter 42 likewise influencing same. With regard to emission energy filters, filters 51 & 53 correspond to first 61 and second 63 emission detectors respectively.

The excitation filters of the photometer, which advantageously comprise band pass interference filters, are generally characterized as follows: the design bandwidth of filter 31 is preferably shorter than beam splitter 40; the design bandwidth of filter 32 is preferably longer than beam splitter 40 and shorter than beam splitter 41; and, the design bandwidth of filter 33 is preferably shorter than beam splitter 43. The emission filters, likewise advantageously comprised of band pass interference filters, are generally characterized as follows: the design bandwidth of filter 51 is preferably longer than beam splitter 41, and shorter than beam splitter 42; and, the design bandwidth of filter 53 is preferably longer than beam splitter 43.

The excitation and emission filters must provide strong mutual blocking, where: filter 31 is designed to strongly block filters 51 and 53; filter 32 is designed to strongly block filters 51 and 53; filter 33 is designed to strongly block filters 51 and 53; filter 51 is designed to strongly block filters 31, 32, and 33; and, filter 53 is designed to strongly block filters 31, 32, and 33. The excitation and emission filter ranges are based upon the spectrum of each fluorophore sought for detection. Preferably the excitation and emission spectral peaks coincide with the bandwidth of the filters.

The excitation beam splitters of the photometer, which advantageously comprise long pass dichroic mirrors, are generally characterized as follows: the design wavelength of beam splitter 41 is longer than beam splitter 40; and, the design wavelength of beam splitter 42 is longer than beam splitter 41; and, the design wavelength of beam splitter 43 is longer than beam splitter 42.

In light of the foregoing, and with particular reference to FIG. 4, an outline of optical paths associated with the multi-dye fluorescence photometer follows. Generally, fluorophore excitation paths begin at the fluorophore excitation sources and end at the target, with fluorophore emission paths commencing at the target and terminating at the emission detector, more particularly:

As to the first fluorophore, a first excitation energy is emitted from first fluorophore excitation source 21, through excitation filter 31 for reflection by beam splitter 40 and further reflection by beam splitter 41 so as to thereafter pass through objective lens 15 and on to sample 12 whereupon the first fluorophore emits emission energy back through objective lens 15, through beam splitter 41 for reflection by beam splitter 42, through emission filter 51 and to detector or sensor 61;

As to the second fluorophore, a second excitation energy is emitted from second fluorophore excitation source 22 through excitation filter 32 and beam splitter 40 for reflection by beam splitter 41 through objective lens 15, and to sample 12 whereupon the second fluorophore emits emission energy back through objective lens 15, through beam splitter 41 for reflection by beam splitter 42, through emission filter 51 and to detector or sensor 61;

As to the third fluorophore, a third excitation energy is emitted from third fluorophore excitation source 23 through excitation filter 33 for reflection by beam splitter 43 and passage through beam splitter 42 and beam splitter 41 through objective lens 15, and to sample 12 whereupon the third fluorophore emits emission energy back through objective lens 15, through beam splitters 41, 42, & 43, through emission filter 53, and to detector or sensor 63.

Prior to a presentation of the scanning process, one or more operational modalities of the apparatus, and/or methods of the subject disclosure, several concluding particulars with regard to select elements or structures of the multi-dye fluorescence photometer are warranted. Specifics as to the fluorophore excitation sources, the filters, the beam splitters, the emission detectors, and the objective lens follows, with a concluding identification of select attendant structures of the fluorophore excitation sources and the beam splitters.

First, in connection to the fluorophore excitation sources, first second and third sources are advantageously comprised of light emitting diodes (LEDs), more particularly designated, for example and without limitation, as follows: first fluorophore excitation source 21 comprises a 505 nm center wavelength FAM excitation lamp, e.g., part no. OSRAM LV W5SN-JXKZ-25-S-Z from OSRAM GmbH, Germany; second fluorophore excitation source 22 comprises a 528 nm center wavelength VIC excitation lamp, e.g., OSRAM LT W5SN-JYKZ-36-Z from OSRAM GmbH, Germany; and, third fluorophore excitation source 23 comprises a 590 nm center wavelength ROX excitation lamp, e.g., part no. OSRAM LY W5SN-JYKY-46-Z from OSRAM GmbH, Germany.

Second, in connection to the band pass interference filters, the following specifications are noted for each of excitation filters 31, 32 and 33 respectively: center wavelength 485, with a bandwidth of 20 (i.e., 485/20); 520/10; and, 590/20. With regard to the emission filters, namely emission filters 51 & 53, specifications therefore are 550/20 and 620/20 respectively.

Third, with regard to the beam splitters, the following specifications are noted for each of beam splitters 40, 41, 42 and 43 respectively: center wavelength 510, long pass (i.e., 510LP); 535LP; 570LP; and, 605LP.

Fourth, with regard to the emission detectors, first and second emission detectors are advantageously comprised of photomultiplier tubes (PMTs), more particularly designated, for example without limitation, the H5784 series of metal package PMT products of Hamamatsu Photonics K.K., Japan.

Fifth, with regard to objective lens 15, a Plan Fluor series lens of the CFI60 family of "objectives for biological microscopes" from Nikon Instruments, Inc., New York, U.S.A. is particularly well suited for passage of the excitation and emission energy in the context of the previously described components.

Figure 5:
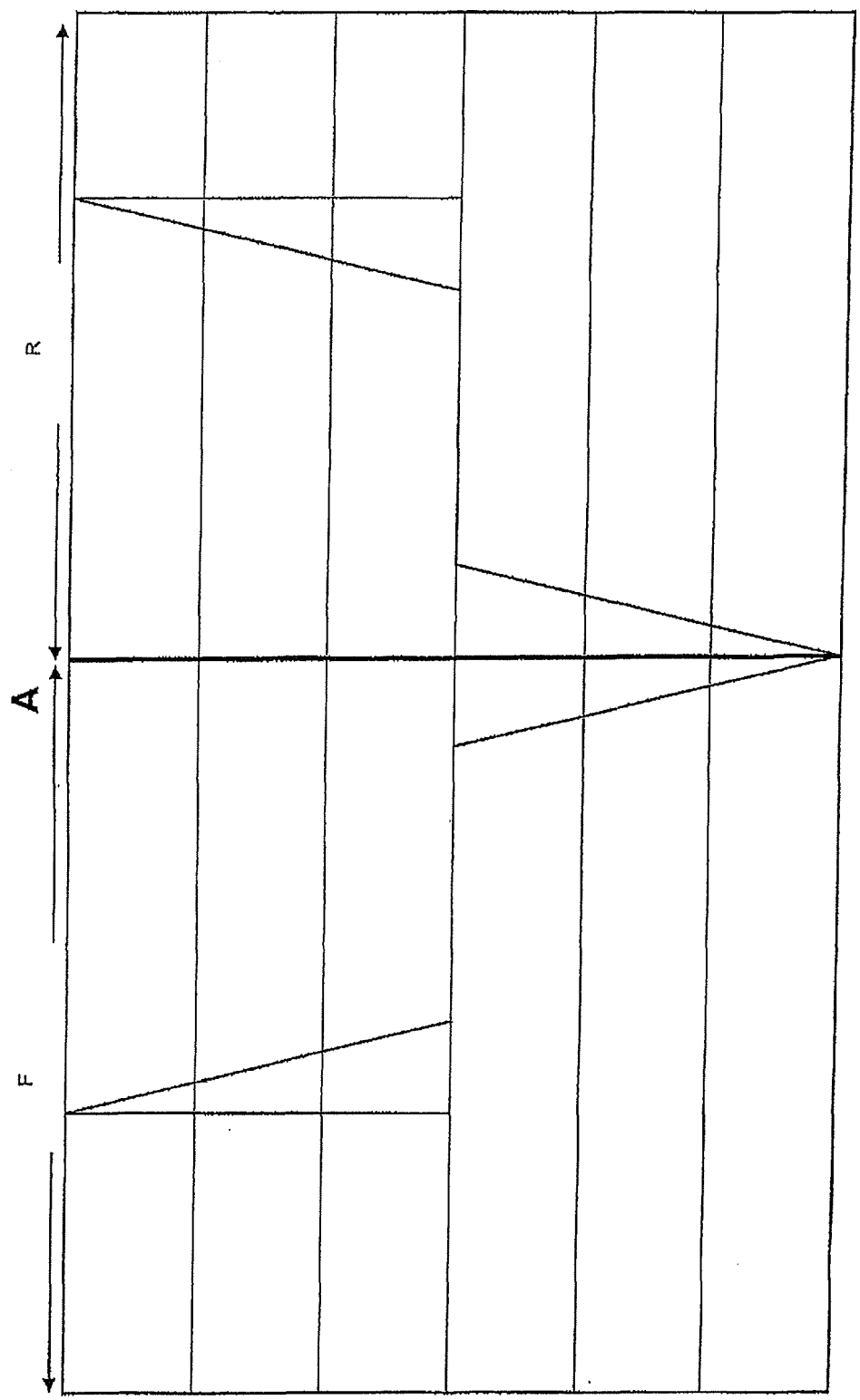

Lastly, and with continued reference to FIGS. 4 & 5 as the circumstance warrants, in as much as the fluorophore excitation sources generally comprise a source of excitation energy in the form of an LED or the like, a housing 24 for containing and directing the excitation energy, and a heat sink 25 operatively linked to the LED is provided. Moreover, in as much as the beam splitters generally comprise long pass dichroic mirrors (FIG. 4), a beam splitter body 45, more particularly a two part body as shown, and an optical beam dump structure 46 are likewise provided.

Recalling threshold issues of running the scanner through its paces, e.g., moving from point A to B and back to A, and the ever present need to gather data during the journey, operational modalities with regard to the subject scanning photometer scanning apparatus, and, as the case may be, the subject multi-dye fluorescence photometer are generally directed to the minimization of uncertainty with regard to data/information gathered by the scanning operation. The presentation of a preferred process of directing the scanning photometer in relation to the arrayed targets precedes a presentation of operational steps with regard to optical operational modalities for the multi-dye fluorescence photometer.

In the preferred embodiment, the scanning cycle is composed of two moves: the carriage first moves a given distance in a first direction, and then moves in the reverse direction, back to the starting position, whereupon the cycle repeats. As previously noted, in the context of the foregoing description and semantic, a select column of arrayed targets is scanned in the first direction, and a column of targets adjacent the select column is scanned in the reverse direction. Each target of the targets of the column is read during the zero acceleration (i.e., constant velocity) portion of the motion profile.

The key to having a minimum jerk move is to avoid torque discontinuities, with the key to minimization of the magnitude of the jerk being to maintain the torque from the end of the forward move (F) to the start of the reverse move (R). In the light of the instant teaching, the direction change is not accompanied by the customary force change to the motor shaft. The force on the shaft never goes to zero during direction change between F and R, see e.g., the motion (i.e., acceleration) profile of FIG. 5 corresponding to the scanning photometer of the instant invention. Jerk assessment parameters comprise the following: (1) the constant velocity of the carriage at which the target is read; (2) the average acceleration; (3) the average deceleration; and, (4) the shape of the triangular acceleration curve.

The carriage according to the teaching of the present invention can now be operated at significantly higher speeds with minimum jerk, and the corresponding or resulting reduction of vibration. It is to be further noted that the profile of FIG. 5 also lends itself to other curves or shapes such as sinusoidal functions.

Thus, the motion profile according to the teaching of the present invention reduces vibration due to high-jerk acceleration and deceleration in the optical reader as it moves across the target. The motion profile allows the carriage that carries the optical reader to scan the target at high velocities, while minimizing jerk. Moreover, making the system mechanically rigid to minimize deflections, and choosing a high-resolution servo mechanism to allow accurate positioning aid in greatly reducing the drawbacks of a moveable optical reader.

Turning now to the preferred optical operational modalities for the multi-dye fluorescence photometer, multi-dye measurements characterized by notions of colocalization, consensing, consituational, and confocal are noted. A brief summary of each follows.

An advantage according to the preferred teaching of the present invention is "colocalized (i.e., the same location) multi-dye measurement." A primary goal of the scanner is to measure an accurate ratio of multiple fluorophores present within the sample or target. It is of secondary importance to measure the absolute quantity of each fluorophore within the sample. The relative spatial intersection of the photometer optical path with the sample to be measured can have a significant influence on both the excitation energy imparted into the sample, and the collection of the resulting emission. Therefore, the alignment between multiple fluorophore excitations and emissions has a considerable influence on the measured signal strength. One solution directed to this issue is to combine multiple excitation and emission optical paths through a common objective lens. With this approach, independent measurements may be taken simultaneously at a common localized alignment, or in very rapid succession by flashing the excitation lamps, effectively at one alignment.

A further advantage according to the preferred teaching of the present invention is "consensory (i.e., cosensing using the same sensor) contemporal (i.e., at the same time) multi-dye measurement." A primary goal of the scanner is to measure an accurate ratio between first and second select fluorophore emissions. As emission sensors may exhibit a unique signal drift, warm-up, or other non-linear behavior, unwelcome uncertainty is inherent in the dedicated detection of first and second select fluorophore emissions with first and second emission detectors. By using a single sensor to measure both first and second select fluorophore emissions, a more accurate ratio is possible.

In the current state of the art, a single sensor is used (i.e., the notion of consensory) via scanning an entire array to measure emissions from a first fluorophore, then, subsequent to switching optical filter elements, another repeat scan of the array is conducted. With this approach, however, the drift of the sensor will not be the same between passes. This difference will introduce an error in the ratio between the readings for each sample. In contrast, by quickly "switching" the excitation lamps, the sensor drift will effectively be the same value at that moment (i.e., consensory plus contemporal). When the same error is applied to two measurements, a more accurate ratio is provided. By quickly switching excitation sources, both fluorophore emissions are detected/measured independently by the same/common sensor, and at very short (i.e., not meaningful) time intervals. This approach provides measurements that effectively cancel out the sensor drift.

Yet a further advantage according to the preferred teaching of the present invention is "consitutational (i.e., the same situation or circumstance of the target/specimen/sample) multi-dye measurement." In the current state of the art, the samples are moved while the photometer remains stationary to perform a first measurement. As should be readily appreciated, the sample is plainly at risk of being in a different situational relationship or inherent condition between measurements, i.e., at measurement "1" the sample is in a first situation, and at measurement "2," the sample is at a second situation, wherein the first and second situations are not interchangeable equivalents. Moreover, it is to be appreciated that there may exist scenarios where the specimen, advantageously residing in a sub-microliter liquid reaction volume (i.e., a well) of the array media, undergoes time dependent or independent changes, physical or otherwise. For example, and without limitation, there is the potential for the fluorophore to float about freely within a well during the intervening time between scans. With the current approach, the samples remain stationary while all the measurements are performed in very rapid succession, effectively at the same physical situation or circumstance.

Still further, an advantage according to the preferred teaching of the present invention is "confocal (i.e., the same focus) multi-dye measurement." By using an aperture in the emission energy path, scattered light emitted by the sample can be rejected, and only the light emitted at the focal point of the objective lens can be collected by the sensor. This approach represents a stronger and/or more precise form of colocalized measurement. Multiple individual apertures can be used for each sensor, or a common single aperture may be placed in the combined beam paths.

With regard to preferred, non-limiting method or process particulars which follow, namely, photometric scanning methods, it is to be understood that a preferred scanning context is array scanning. Whether the arrayed targets are embodied in an array tape or a plate, characteristic of the media carrying, holding, retaining, etc. the objects for scanning is a series of spaced apart targets, more particularly, a series of spaced apart target columns. Thus, both tape scanning, via a tape scanning region, and plate scanning, via a plate scanning region, alone or in combination, are contemplated and believed advantageous. Moreover, and consistent with the subject disclosure, it is to be understood that scanning entails moving an optical reader/reader head, more particularly, a photometer, in relation to the arrayed targets, arrayed targets which likewise may be indexed selectively advanced), either from one column to the next, or some other select increment subsequent to an initial pass of the photometer.

Photometric scanning methods of the instant invention may be fairly and generally characterized by the steps of passing an objective lens across a series of spaced apart targets, and transmitting energy from at least two fluorophore excitation sources through an optical path of the objective lens for receipt by a target of the series of spaced apart targets in furtherance of exciting at least two fluorophores of the target. Advantageously, but not necessarily, the objective lens is passed across the series of spaced apart targets at a constant velocity. Moreover, during a "pass," energy transmissions directed to the target from the fluorophore excitation sources may be simultaneous, periodic, alternated (i.e., transmission from a first source, transmission from a second source upon termination of the first source transmission, and a return to first source transmission upon termination of the second source transmission), or pulsed (i.e., transmission from one source of the two sources is pulsed during the energy transmission of another of the two sources).

As previously noted, a further operative advantage is obtained via cosensing. More particularly, a preferred photometric scanning method further includes or is characterized by the detection, via a single emission detector, of two fluorophore emissions corresponding to the excitation of the two fluorophores of the target. To the extent that greater than two emission energies are to be detected, e.g., three as is characteristic of allele specific PCR assays, steps associated with a further excitation energy source and corresponding emission detector are likewise contemplated.

Lastly, with regard to or even apart from the aforedescribed scanning photometer apparatus, and subassemblies therefore, optical operational modalities, and photometric scanning methodologies, further modifications or departures are to be noted. For example, the optical reader/read head may advantageously include more than one photometer. In a read head so configured, each photometer may be aimed or otherwise directed towards different targets or target groups/subsets. Moreover, the photometers may be operatively aligned with regard to the same column of the arrayed targets. Further still, a calibration functionality is enabled in that the utilization of multiple photometers/photometer channels to detect/measure the same target in furtherance of comparative assessment of the findings, with correction methods, thereafter and as the circumstances warrant, applied such that each photometer "reports" the same signal for the same target. Yet further, multiple scanning rails may be provided such that an array tape or the like feeds continuously through all scanning modules for simultaneous, parallel scanning optical readers for different fluorophores.

Thus, since the structures and/or methods of the scanning photometer disclosed herein may be embodied, in other specific forms without departing from the spirit or general characteristics thereof, some of which forms have been indicated, the embodiments described and depicted herein/with are to be considered in all respects illustrative and not restrictive. Accordingly, the scope of the subject invention is as defined in the language of the appended claims, and includes not insubstantial equivalents thereto.

That which is claimed is:

1. A photometer comprising:
   a first fluorophore excitation source;
   a second fluorophore excitation source;
   an objective lens, characterized by an optical path, through which excitation energy from said first and said second fluorophore excitation sources pass;
   a first emission detector configured and arranged for detecting both a first fluorophore emission originating from excitation of a first fluorophore, and a second fluorophore emission originating from excitation of a second fluorophore; and
   emission energy conditioning elements including at least a first beam splitter and a second beam splitter, the first and second beam splitters positioned to reflect the first excitation energy through the objective lens, and wherein the first beam splitter is configured and arranged to transmit excitation energy from the second excitation source, and wherein the second beam splitter is configured and arranged to reflect the energy from the second excitation source through the objective lens, and is further configured and arranged to transmit the second fluorophore emission received from the objective lens.

2. The photometer of claim 1, in combination with and operatively supported by a scanning rail carriage for reversible travel with respect thereto.

3. The photometer of claim 1, further comprising a third fluorophore excitation source; configured and arranged to enable excitation energy from said third fluorophore excitation source to pass through said objective lens.

4. The photometer of claim 1, further comprising a second emission detector configured and arranged for detecting a third fluorophore emission originating from excitation of a third fluorophore.

5. The photometer of claim 1, further comprising excitation energy conditioning elements operatively interposed between said first and second excitation sources and said objective lens.

6. The photometer of claim 5, wherein said excitation energy conditioning elements comprise excitation filters and at least the first and second beam splitters configured and arranged for select passage of excitation energy to and along said optical path of said objective lens.

7. The photometer of claim 1, wherein said emission energy conditioning elements comprise at least the second beam splitter and a first emission filter configured and arranged for select passage of emission energy to said first emission detector.

8. The photometer of claim 1, further comprising a third beam splitter configured and arranged to enable passage of excitation energy from one of said first a third fluorophore excitation source to the objective lens.

9. The photometer of claim 8, further comprising a fourth beam splitter, configured and arranged to enable reflection of excitation energy from the third fluorophore excitation source and through the third beam splitter to the objective lens.

10. The photometer of claim 1, wherein the emission energy conditioning elements include a second emission filter configured and arranged for select passage of emission energy to the second emission detector.

11. The photometer of claim 1, wherein energy transmission from said first fluorophore excitation source is configured and arranged to be simultaneous with energy transmission from said second fluorophore excitation source.

12. The photometer of claim 1, wherein energy transmission from one of said first fluorophore excitation source and said second fluorophore excitation source is configured and arranged to be periodic.

13. The photometer of claim 1, wherein energy transmission from at least one of said first fluorophore excitation source and said second fluorophore excitation source is configured and arranged to be alternated with energy transmission of another of said first fluorophore excitation source and said second fluorophore excitation source.

14. The photometer of claim 1, wherein energy transmission from at least one of said first fluorophore excitation source and said second fluorophore excitation source is configured and arranged to be pulsed during energy transmission of another of said first fluorophore excitation source and said second fluorophore excitation source.

15. The photometer of claim 1, wherein said optical path of said objective lens is configured and arranged to be directed at and across a series of spaced apart targets.

16. The photometer of claim 1, wherein said objective lens is configured and arranged to be passed across a series of spaced apart targets.

17. The photometer of claim 1, wherein said objective lens is configured and arranged to be passed across a series of spaced apart targets at a constant velocity.

18. The photometer of claim 15, wherein said series of spaced apart targets are embodied in an array tape.

19. The photometer of claim 15, wherein the series of spaced apart targets are embodied in a plate.

20. The photometer of claim 15, wherein the series of spaced apart targets comprise columns of targets.

21. The photometer of claim 15, wherein said objective lens is configured and arranged to pass across a column of columns of targets in a first direction, and thereafter pass across a column of targets adjacent said column in a direction reverse of said first direction.

* * * * *